United States Patent
Hayes

(10) Patent No.: US 9,433,799 B2
(45) Date of Patent: Sep. 6, 2016

(54) PHOTOTHERAPY LIGHTS

(75) Inventor: Stephen Bryce Hayes, Cambridge (GB)

(73) Assignee: Outside In (Cambridge) Ltd. (GB)

( * ) Notice: Subject to any disclaimer, the term of this patent is extended or adjusted under 35 U.S.C. 154(b) by 2480 days.

(21) Appl. No.: 11/651,861

(22) Filed: Jan. 10, 2007

(65) Prior Publication Data
US 2008/0119912 A1 May 22, 2008

(30) Foreign Application Priority Data
Jan. 11, 2006 (GB) .................................. 0600478.2

(51) Int. Cl.
*A61N 5/06* (2006.01)
*A61M 21/00* (2006.01)

(52) U.S. Cl.
CPC ............ *A61N 5/0618* (2013.01); *A61M 21/00* (2013.01); *A61M 2021/0044* (2013.01); *A61M 2021/0083* (2013.01); *A61N 2005/0652* (2013.01); *A61N 2005/0663* (2013.01)

(58) Field of Classification Search
CPC ............................ A61N 5/062; A61N 5/0616
USPC ..................................................... 607/88–94
See application file for complete search history.

(56) References Cited

U.S. PATENT DOCUMENTS

| 5,343,121 | A | * | 8/1994 | Terman et al. | 315/158 |
| 5,589,741 | A | * | 12/1996 | Terman et al. | 315/360 |
| 5,824,024 | A | | 10/1998 | Dial | |
| 6,554,439 | B1 | * | 4/2003 | Teicher et al. | 362/2 |
| 2003/0231495 | A1 | | 12/2003 | Searfoss, III | |
| 2004/0249423 | A1 | | 12/2004 | Savage | |
| 2006/0064144 | A1 | * | 3/2006 | Chen et al. | 607/90 |
| 2008/0103561 | A1 | * | 5/2008 | Moscovici | 607/88 |
| 2008/0119912 | A1 | * | 5/2008 | Hayes | 607/88 |

FOREIGN PATENT DOCUMENTS

| WO | WO 98/51372 | 11/1998 |
| WO | WO 2006/012123 A2 | 2/2006 |
| WO | WO 2006/087723 A2 | 8/2006 |

OTHER PUBLICATIONS

Prophylactic treatment of seasonal affective disorder (SAD) by using light visors: bright white or infrared light?; Meesters et al.; Society of Biological Psychiatry; Jul. 1999.*
The Phototherapy Light Visor; Teicher et al. The American Journal of Psychiatry. Washington: Aug. 1995.vol. 152, Iss. 8; p. 1197.*
European Search Report for corresponding EP 07 00 0472 completed Feb. 12, 2008 by Joana Büchler Costa.

* cited by examiner

*Primary Examiner* — William Thomson
*Assistant Examiner* — Jeffrey Lipitz
(74) *Attorney, Agent, or Firm* — Tarolli, Sundheim, Covell & Tummino LLP

(57) ABSTRACT

This invention relates to phototherapy lights, in particular for a combination of Bright Light Therapy and Dawn Simulation. A phototherapy light source having two operational modes, a first dawn simulator mode; and a second, bright light therapy mode; the light comprising a controller coupled to a light source; and wherein, in said first mode said light source is controlled to provide variable illumination with a minimum light intensity of less than 1 lux at 50 centimeters, and in said second mode said light source is controlled to provide illumination with a light intensity of at least 1000 lux at 50 centimeters.

9 Claims, 2 Drawing Sheets

PHOTOTHERAPY LIGHTS

RELATED APPLICATIONS

The present application claims priority from GB0600478.2 filed 11 Jan. 2006 of the same title.

TECHNICAL FIELD

This invention relates to phototherapy lights, in particular for a combination of Bright Light Therapy and Dawn Simulation.

BACKGROUND

Two fundamental techniques in phototherapy for chronobiological purposes are Bright Light Therapy and Dawn Simulation. These can be used for the symptomatic relief of inter alia, seasonal affective disorder (SAD), sleep pattern disorders and the like. Dawn Simulator alarm clocks mimic a natural sunrise in the morning and may also mimic a natural sunset. This wakes the user gently and also assists the user to fall asleep at night. We have previously described some improved Dawn Simulators in UK Patent Application Numbers 0501079.8 and 0501076.4, both filed on 19 Jan. 2005. Bright Light Therapy devices aim to simulate a natural level of sunlight such as might be experienced on a Spring morning on a clear day, and thus generally provide an output of at least 1000 lux, often closer to 10,000 lux at a typical distance from the user of around 0.5 meter.

There is, however, a continuing need for improved phototherapy lights.

SUMMARY

According to the present invention there is therefore provided a phototherapy light source having two operational modes, a first dawn simulator mode; and a second, bright light therapy mode; the light comprising a controller coupled to a light source; and wherein, in said first mode said light source is controlled to provide variable illumination with a minimum light intensity of less than 1 lux at 50 centimeters, and in said second mode said light source is controlled to provide illumination with a light intensity of at least 1000 lux at 50 centimeters.

Preferably the light source comprises a plurality of light emitting diodes (LEDs) to provide the illumination in both the first, Dawn Simulator mode and the second, Bright Light Therapy mode. Thus high output LEDs may be employed for the bright light and progressively dimmed and/or switched off in the Dawn Simulator (sunrise/sunset) mode. Alternatively LEDs may be used to provide the lowest light output levels, for example at the onset of dawn simulation, and fluorescent or other discharge sources may be employed for the Bright Light Therapy mode. Such discharge sources may include cold cathode discharge sources and/or external electrode fluorescent lamps (EEFL). However LEDs provide a significant advantage in that a single type of lighting technology may be employed for both the very low light intensities used for dawn simulation, and the very high light intensities used for Bright Light Therapy.

In some preferred embodiments the photo therapy light is configured to change a colour of the illumination in the dawn simulator mode so that the illumination is redder at low levels and becomes progressively "whiter" as the illumination level increases. This aims to provide a more natural simulation of dawn (and/or dusk) and hence provide a greater circadian effect. This may be achieved by employing a light source comprising LEDs of at least two different colours (here a "white" LED is considered as a "colour"), a first colour, and a second colour redder than the first. The phototherapy light may then incorporate a controller configured to control a relative brightness of these different coloured LEDs to alter the colour of the illumination in the dawn simulator mode.

In some preferred embodiments a ratio of the Bright Light Therapy light intensity to the minimum light intensity is at least 1000:1, more preferably 5000:1 or 10000:1. Thus in embodiments the minimum light intensity may be less than 0.1 lux, and the Bright Light Therapy light intensity greater than 1200 lux, 2500 lux or 5000 lux at a typical user distance of around 50 centimeters.

In a related embodiment the invention provides a phototherapy light configured to provide at least two levels of illumination, a first level of illumination and a second, lower level of illumination, and wherein said illumination at said second, lower level is redder than said illumination at said first level.

Where the phototherapy light comprises a Bright Light Therapy light. This is preferably dimmable to a substantially off condition.

The invention further provides a combined Bright Light Therapy device and Dawn Simulator comprising a light source controllable over a brightness range of at least 1000:1.

The invention still further provides a combined Bright Light Therapy device and Dawn Simulator in which the light source comprises a plurality of light emitting diodes.

In embodiments a phototherapy light as described above has at least one mode in which substantially no light output is provided in a wavelength range below 560 nm (which approximately corresponds to a green/yellow colour).

In a still further aspect the invention provides a phototherapy light having at least one mode in which the light output is sufficient for Bright Light Therapy, for example for treating SAD, the phototherapy light also being adjustable in colour, in particular to provide room or other lighting which has substantially no circadian effect.

The invention further provides a method of using a phototherapy light as described above to treat seasonal affective disorder, in particular by operating the light in both a Dawn Simulator mode and a Bright Light Therapy mode.

BRIEF DESCRIPTION OF THE DRAWINGS

These and other aspects of the invention will now be further described by way of example, with reference to the accompany figures in which.

DETAILED DESCRIPTION

Figure 1:
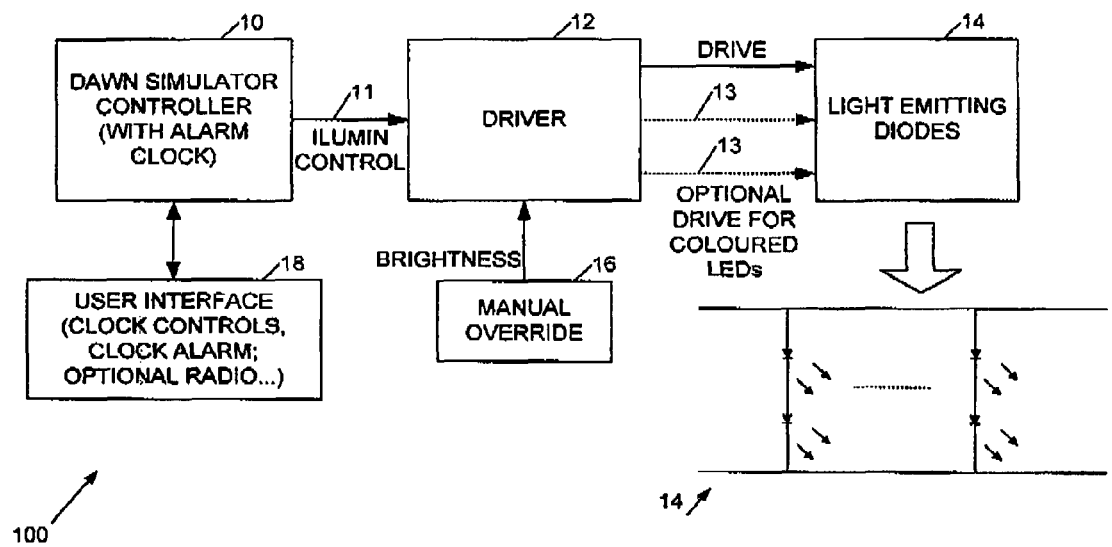
FIG. 1 shows a block diagram of an embodiment of the invention.

Referring first to FIG. 1, an example combined Dawn Simulator and Bright Light Therapy apparatus 100 comprises a Dawn Simulator controller 10 typically comprising an alarm clock in which prior to the alarm time an illumination control output controls illumination to gradually ramp to a maximum level (at which time, for example, a radio might also be switched on). The illumination control signal is provided to a driver 12, for example employing pulse width modulation, which provides a drive output to a plurality of light emitting diodes responsive to the illumination control signal 11.

The LEDs are both serial and parallel connected, as shown in the inset to the figure. Optionally driver 12 may provide a plurality of drive outputs, in particular colour drive outputs 13 for changing an illumination colour of the phototherapy light, as described further below.

Figure 2A:
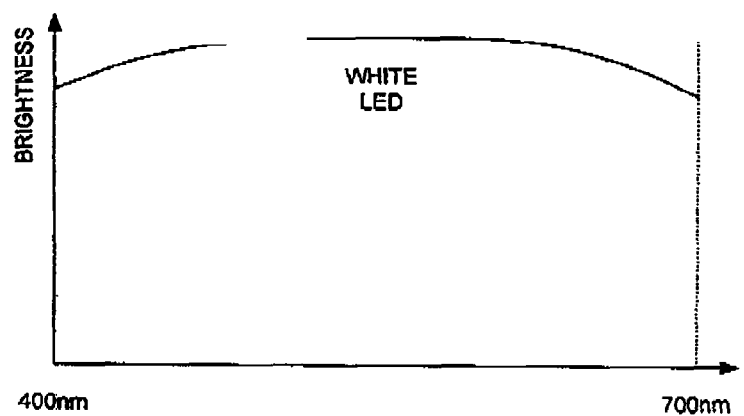
FIGS. 2a and 2b show example spectral outputs of the device of FIG. 1.

In one embodiment primarily white LEDs are employed with a typical spectrum as shown in FIG. 2a. Examples of suitable LEDs are the Nichia NSPW500BS (around 25 of these may be used to give a suitable Bright Light Therapy output) and/or LEDs in the Lumiled Luxeon range (5 or more of these may be employed to provide sufficient light output for Bright Light Therapy).

Referring again to FIG. 1, the apparatus also includes a manual override 16 for manual control of the brightness of the LEDs 14, and a user interface 18 to provide controls for the Dawn Simulator, for example, clock, alarm and radio controls.

Figure 2B:
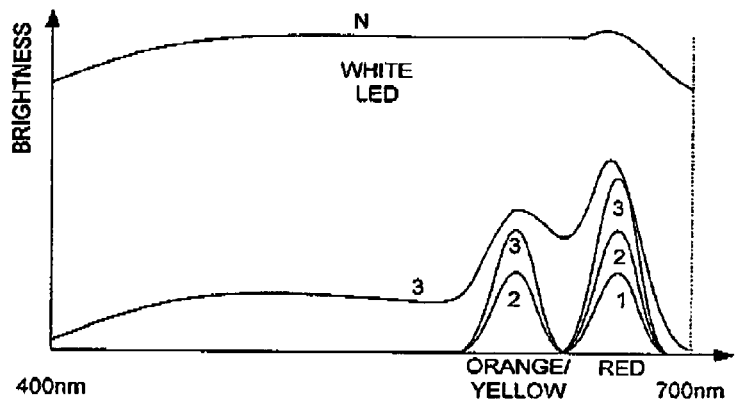

Referring now to FIG. 2b, the LEDs 14 may include one or more coloured LEDs, for example a set of one or more high output red LEDs and, optionally, a further set of one or more high output orange/yellow LEDs. These are controlled by driver 12 in conjunction with the white LEDs so that at low light levels substantially only the red LEDs are on, the orange/yellow and white LEDs being progressively turned on as the overall desired light output increases. This is indicated schematically in FIG. 2b by the labels, 1, 2, 3 . . . N, which indicate progressively increasing overall light output levels from the apparatus 100.

Figure 3:
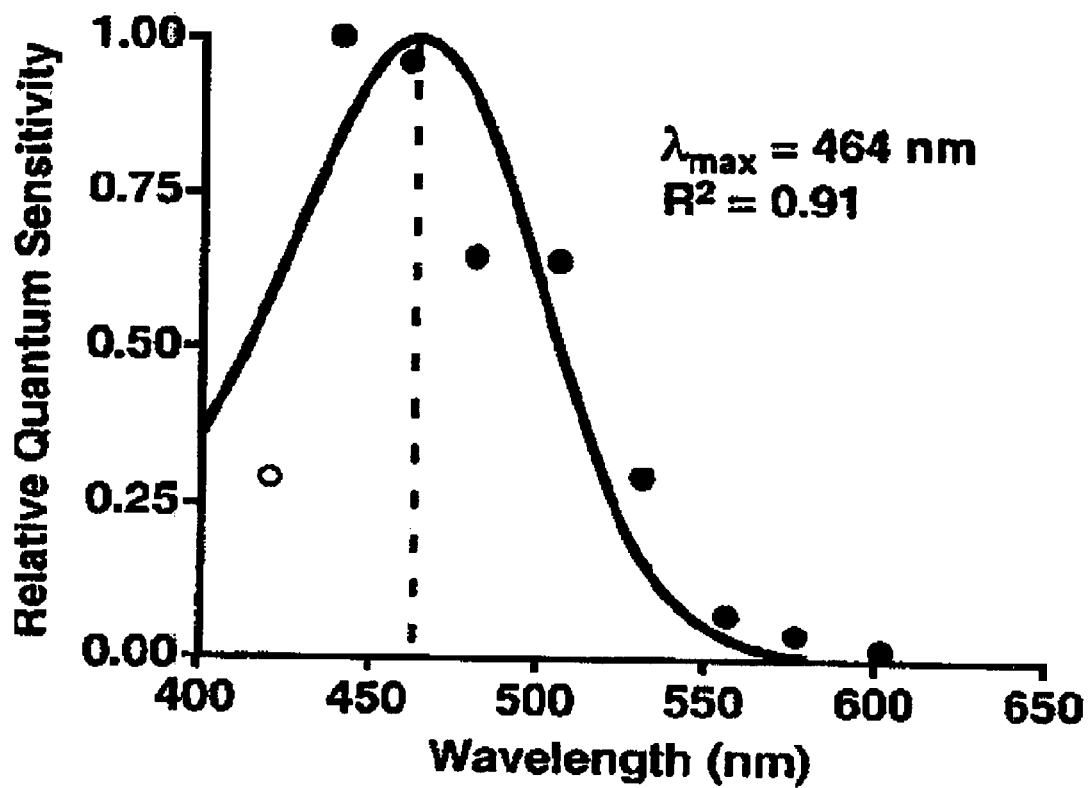
FIG. 3 shows a human melatonin suppression response.

Recent research in the field of Bright Light Therapy has indicated that certain parts of the visible spectrum, centred around approximately 470 nm —deep blue, have a greater circadian effect than other parts of the visible spectrum, in particular yellow/orange/red, above 560 nm. A possible mechanism for this response is illustrated in FIG. 3, which shows the results of an experiment indicating levels of melatonin suppression under different illumination wavelengths. Advantageously, therefore, the colour of the phototherapy light is varied during the dawn simulation process. This may be achieved, as indicated above, by using LEDs of different colours, selectively powering these LEDs so that the combined output progressively varies from dull red at the onset of the dawn simulation towards a colour more typical of daylight sunshine. Alternatively LEDs which are able to change colour (RGB-LEDs) may be employed.

In embodiments the Bright Light Therapy device may have a colour temperature greater than 5000K to provide a "cool" light source.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A phototherapy light source having two operational modes,
   a first dawn simulator mode; and
   a second, bright light therapy mode;
   the light comprising:
   a light source comprising a plurality of light emitting diodes of different colours, said plurality of light emitting diodes being arranged to progressively vary an emitted spectrum of light from a first spectrum to a second spectrum, and
   a controller coupled to a light source; and
   wherein, in said first mode said light source is controlled to provide variable illumination with a minimum light intensity of less than 1 lux at 50 centimeters, and in said second mode said light source is controlled to provide illumination with a light intensity of at least 1000 lux at 50 centimeters,
   said first spectrum has dull red light spectrum, and
   said second spectrum has a colour of typical daylight sunshine and has greater overall intensity than the first spectrum, and wherein
   said phototherapy light source is arranged to provide in said first dawn simulator mode an illumination mode in which light from said light emitting diodes has substantially no light output below 560 nm,
   the phototherapy light configured to change a colour of said illumination in said dawn simulator mode such that the said illumination is redder at a lower illumination level than at a higher illumination level.

2. A phototherapy light as claimed in claim 1 wherein said light source comprises LEDs of at least two different colours, a first colour and a second colour redder than said first colour and wherein said controller is configured to control a relative brightness of said different coloured LEDs to alter the colour of said illumination in said variable illumination dawn simulator mode.

3. A phototherapy light as claimed in claim 1 wherein said light source comprises a plurality of light emitting diodes (LEDs) to provide said illumination in said bright light therapy mode, dimmable to provide said variable illumination.

4. A phototherapy light a claimed in claim 1 wherein said light source comprises at least one LED and at least one discharge light source; and wherein said controller is configured to use said at least one LED for said first dawn simulator mode and said discharge light source for said bright light therapy mode.

5. A phototherapy light as claimed in claim 1 wherein a ratio of said bright light therapy light intensity to said minimum light intensity in at least 1000:1.

6. A phototherapy light, said phototherapy light comprising a plurality of light emitting diodes of different colours, said light emitting diodes configured to provide at least two levels of illumination, a first level of illumination and a second, lower level of illumination with a light intensity of less than 1 lux at 50 centimeters, and wherein said illumination of said second, lower level is redder than said illumination at said first level, said plurality of light emitting diodes being arranged to progressively vary an emitted spectrum of light from a first spectrum having said second illumination level to a second spectrum having said first illumination level, wherein said first spectrum is a dull red light spectrum, and said second spectrum has a colour of typical daylight sunshine and has greater overall intensity than the first spectrum, and wherein said progressive variation of said phototherapy light has an illumination mode in which light from said light emitting diodes has substantially no light output below 560 nm, the phototherapy light configured to change a colour of said illumination in a dawn simulator mode such that the said illumination is redder at a lower illumination level than at a higher illumination level.

7. A phototherapy light as claimed in claim 6 wherein said phototherapy light is a dawn simulator configured to progressively vary said illumination from said second lower level to said first level.

8. A phototherapy light as claimed in claim 6 wherein said phototherapy light is a bright light therapy light and wherein said first level of illumination is at least 1000 lux at 50 centimeters.

9. A phototherapy light as claimed in claim 6 comprising a controller and light source including LEDs of at least two different colours, a first colour and a second colour redder than said first colour, and wherein said controller is configured to control a relative brightness of said different coloured LEDs for said first and second illumination levels.

* * * * *